US010588569B2

(12) United States Patent
Kwon et al.

(10) Patent No.: US 10,588,569 B2
(45) Date of Patent: Mar. 17, 2020

(54) CONDUCTIVE FABRIC

(71) Applicant: TOYOBO CO., LTD., Osaka (JP)

(72) Inventors: Euichul Kwon, Shiga (JP); Sonoko Ishimaru, Shiga (JP); Naruhiro Shiozawa, Shiga (JP); Jihyoung Lee, Shiga (JP)

(73) Assignee: TOYOBO CO., LTD., Osaka (JP)

( * ) Notice: Subject to any disclaimer, the term of this patent is extended or adjusted under 35 U.S.C. 154(b) by 3 days.

(21) Appl. No.: 15/543,295

(22) PCT Filed: Jan. 14, 2016

(86) PCT No.: PCT/JP2016/050936
§ 371 (c)(1),
(2) Date: Jul. 13, 2017

(87) PCT Pub. No.: WO2016/114339
PCT Pub. Date: Jul. 21, 2016

(65) Prior Publication Data
US 2018/0028115 A1   Feb. 1, 2018

(30) Foreign Application Priority Data
Jan. 14, 2015   (JP) ................................ 2015-005384

(51) Int. Cl.
*A61B 5/00*  (2006.01)
*A61B 5/0478*  (2006.01)
*A61B 5/0492*  (2006.01)
*H01B 1/22*  (2006.01)
*A61B 5/0408*  (2006.01)
*B32B 7/02*  (2019.01)
*H01B 5/14*  (2006.01)
*A61B 5/01*  (2006.01)
*A61B 5/024*  (2006.01)
*A61B 5/08*  (2006.01)

(52) U.S. Cl.
CPC ............. *A61B 5/6804* (2013.01); *A61B 5/01* (2013.01); *A61B 5/02438* (2013.01); *A61B 5/0408* (2013.01); *A61B 5/0478* (2013.01); *A61B 5/04085* (2013.01); *A61B 5/0492* (2013.01); *A61B 5/0816* (2013.01); *A61B 5/4266* (2013.01); *B32B 7/02* (2013.01); *H01B 1/22* (2013.01); *H01B 5/14* (2013.01); *A61B 2562/125* (2013.01)

(58) Field of Classification Search
USPC ....................................................... 361/749
See application file for complete search history.

(56) References Cited

U.S. PATENT DOCUMENTS

| 6,309,563 | B1 | 10/2001 | Iino et al. |
| 10,119,045 | B2 | 11/2018 | Kondo et al. |
| 2003/0054165 | A1 | 3/2003 | Yamanaka et al. |
| 2005/0095406 | A1 | 5/2005 | Gunzel et al. |
| 2005/0277826 | A1 | 12/2005 | Dunseath, Jr. |
| 2007/0119539 | A1 | 5/2007 | Gunzel et al. |
| 2008/0312523 | A1 | 12/2008 | Dunseath |
| 2009/0054758 | A1 | 2/2009 | Dunseath |
| 2009/0117362 | A1 | 5/2009 | Schosseler et al. |
| 2010/0234715 | A1* | 9/2010 | Shin ..................... A61B 5/0402 600/388 |
| 2010/0255742 | A1* | 10/2010 | Yun ........................ H05K 1/056 442/117 |
| 2012/0119626 | A1 | 5/2012 | Takahashi et al. |
| 2012/0152599 | A1* | 6/2012 | Kitagawa ............... H05K 3/381 174/257 |
| 2013/0019383 | A1 | 1/2013 | Korkala et al. |
| 2013/0056249 | A1 | 3/2013 | Taguchi et al. |
| 2013/0225966 | A1 | 8/2013 | Maciá Barber et al. |
| 2013/0338472 | A1 | 12/2013 | Maciá Barber et al. |
| 2014/0124257 | A1 | 5/2014 | Yoshihara et al. |
| 2014/0202744 | A1 | 7/2014 | Kobayashi et al. |
| 2014/0291589 | A1 | 10/2014 | Hata et al. |
| 2014/0318699 | A1 | 10/2014 | Longinotti-Buitoni et al. |
| 2015/0204697 | A1 | 7/2015 | Taguchi et al. |
| 2016/0130471 | A1 | 5/2016 | Burrows et al. |
| 2017/0002181 | A1 | 1/2017 | Lehmann et al. |
| 2017/0188949 | A1 | 7/2017 | Maciá Barber et al. |
| 2017/0224241 | A1* | 8/2017 | Kuwabara ............ A61B 5/0404 |
| 2017/0296123 | A1 | 10/2017 | Maciá Barber et al. |
| 2018/0020936 | A1 | 1/2018 | Kwon et al. |
| 2019/0077930 | A1 | 3/2019 | Irie et al. |

FOREIGN PATENT DOCUMENTS

| CN | 201524078 | 7/2010 |
| CN | 102483972 | 5/2012 |
| EP | 0 892 027 | 1/1999 |
| JP | 6-263899 | 9/1994 |
| JP | H10-95962 | 4/1998 |

(Continued)

OTHER PUBLICATIONS

Extended European Search Report dated Jul. 19, 2018 in corresponding European Application No. 16737369.5.

(Continued)

*Primary Examiner* — Andargie M Aychillhum
(74) *Attorney, Agent, or Firm* — Wenderoth, Lind & Ponack, L.L.P.

(57) ABSTRACT

A conductive fabric including a fabric and a wiring provided on the fabric, wherein the wiring has a first insulating layer formed on the fabric, a conductive layer provided on the first insulating layer, and a second insulating layer provided on the conductive layer, and wherein in a stretching test in which the conductive fabric is stretched by a stretching rate of 10% in a stepwise manner up to a stretching rate of 100% in a longitudinal direction of the wiring, a resistance change ratio when stretched at a stretching rate of 100% is 100-fold or less, the resistance change ratio when stretched at a stretching rate of 100% being represented by an equation: $R_{100}/R_0$ (fold), where $R_0$ is a resistance value at a stretching rate of 0% and $R_{100}$ is a resistance value when stretched at a stretching rate of 100%. The conductive fabric is capable of maintaining high electrical conductivity even upon being stretched.

5 Claims, No Drawings

(56) References Cited

FOREIGN PATENT DOCUMENTS

| | | |
|---|---|---|
| JP | 20000-133055 | 5/2000 |
| JP | 2001-126541 | 5/2001 |
| JP | 2004-288956 | 10/2004 |
| JP | 2004-288957 | 10/2004 |
| JP | 2007-509779 | 4/2007 |
| JP | 2007-173226 | 7/2007 |
| JP | 2007-263833 | 10/2007 |
| JP | 2008-501453 | 1/2008 |
| JP | 2008-198425 | 8/2008 |
| JP | 2010-189795 | 9/2010 |
| JP | 2011-15817 | 1/2011 |
| JP | 2012-33674 | 2/2012 |
| JP | 2012-54192 | 3/2012 |
| JP | 2012-138260 | 7/2012 |
| JP | 2012-183302 | 9/2012 |
| JP | 3178230 | 9/2012 |
| JP | 2012-231018 | 11/2012 |
| JP | 2012-248399 | 12/2012 |
| JP | 2013-135358 | 7/2013 |
| JP | 2013-184024 | 9/2013 |
| JP | 5448736 | 3/2014 |
| JP | 2014-510596 | 5/2014 |
| JP | 2014-137860 | 7/2014 |
| JP | 2014-151018 | 8/2014 |
| JP | 2014-200559 | 10/2014 |
| JP | 2014-228507 | 12/2014 |
| WO | 2011/145411 | 11/2011 |
| WO | 2012/108502 | 8/2012 |
| WO | 2013/031958 | 3/2013 |
| WO | 2013/146254 | 10/2013 |
| WO | 2014/153896 | 10/2014 |
| WO | 2014/178207 | 11/2014 |
| WO | 2016/114298 | 7/2016 |

OTHER PUBLICATIONS

Office Action dated Aug. 7, 2018 in corresponding Japanese Application No. 2016-569476, with English translation.
Paul et al., "An investigation into the durability of screen-printed conductive tracks on textiles", Measurement Science and Technology, 25:1-11 (2014).
Third Party Observation submitted Feb. 14, 2017 in corresponding International (PCT) Application No. PCT/JP2016/050936, with English Translation.
Inoue et al., "Application of Printing Process to Fabrication of E-textiles", Journal of the Surface Finishing Society of Japan, 64(11):577-581 (2013), with Partial English Translation.
International Search Report dated Apr. 19, 2016 in International (PCT) Application No. PCT/JP2016/050819.
Third Party Observation submitted Feb. 2, 2017 in International (PCT) Application No. PCT/JP2016/050819, with English Translation.
International Search Report dated Mar. 29, 2016 in corresponding International (PCT) Application No. PCT/JP2016/050936.
Submission of Information by Third Parties dispatched on Sep. 12, 2017 in Japanese Application No. 2016-569476, with English translation.
Submission of Information by Third Parties dispatched on Sep. 12, 2017 in Japanese Application No. 2016-569498, with English translation.
Japanese Office Action dated Feb. 12, 2019 in corresponding Japanese patent application No. 2018-039115, with English translation.
Office Action dated Mar. 5, 2019 in Japanese Patent Application No. 2018-039116, with English translation.
Office Action dated Mar. 5, 2019 in Japanese Patent Application No. 2018-039119, with English translation.
Office Action dated Mar. 12, 2019 in Japanese Patent Application No. 2018-039117, with English translation.
Office Action dated Nov. 27, 2018 in corresponding Japanese patent application No. 2018-011962, with English translation.
Decision of Rejection dated Dec. 4, 2018 in corresponding Japanese patent application No. 2016-569476, with English translation.
Tada Yasunori, "A Characteristic Evaluation of an Undershirt for Measurement of Bioelectricity Using Conductive Ink Wires", Journal of textile Engineering, Jul. 2013, vol. 59, No. 6, p. 141-148.
Office Action dated Feb. 26, 2019 in corresponding Japanese patent application No. 2018-039114, with English Translation.
European Office Action dated Apr. 18, 2019 in corresponding European patent application No. 16737369.5.
Office Action dated May 29, 2018 in Japanese Application No. 2016-569498, with English translation.
Office Action dated May 28, 2019 in corresponding Japanese Patent Application No. 2018-166995, with English Translation.
Office Action dated Jun. 4, 2019 in corresponding Japanese Patent Application No. 2018-011962, with English Translation.
International Search Report dated Apr. 18, 2017 in International (PCT) Application No. PCT/JP2017/000499.
Ahn et al., "Stretchable electronics: materials, architectures and integrations", Journal of Physics D: Applied Physics, vol. 45, 2012, 103001, pp. 1-14.
Chun et al., "Highly conductive, printable and stretchable composite films of carbon nanotubes and silver", Nature Nanotechnology, vol. 5, Dec. 2010, pp. 853-857.
Office Action dated Aug. 27, 2019 in corresponding Chinese Application No. 2018-166996, with English translation.
Office Action dated Nov. 4, 2019 in corresponding Chinese Patent Application No. 201680005764.7 with English translation.
Communication pursuant to Article 94(3) dated Nov. 5, 2019 in corresponding European Patent Application No. 16737369.5.
Notification of Reasons for Refusal dated Nov. 26, 2019 in corresponding Japanese Application No. 2018-039114, with English translation.
Notification of Reasons for Refusal dated Nov. 26, 2019 in corresponding Japanese Application No. 2018-166995, with English translation.
Extended European Search Report dated Nov. 21, 2019 in corresponding European Application No. 17738393.2.
Notice of Reasons for Refusal dated Dec. 3, 2019 in corresponding Japanese Application No. 2018-039116, with English translation.
Notice of Reasons for Refusal dated Dec. 3, 2019 in corresponding Japanese Application No. 2018-039119, with English translation.

* cited by examiner

CONDUCTIVE FABRIC

TECHNICAL FIELD

The present invention relates to a conductive fabric useful for a wearable biological information measurement device capable of measuring biological information such as electrocardiogram, respiration rate, sweating, body temperature, elbow angle (an amount of exercise), and the like by being worn as a garment.

BACKGROUND ART

Recently, wearable biological information measurement devices capable of easily measuring biological information such as electrocardiogram by being worn as a garment have attracted attention in the medical field and the health monitoring field. For example, a user of a wearable measurement device for measuring electrocardiogram can easily understand the change of heart rate in a variety of situations in daily life by spending a day while wearing it as a garment.

Such a wearable biological information measurement device generally has electrodes, sensors corresponding to various measurements, and a wiring for transmitting those electrical signals to an arithmetic-processing unit or the like inside a garment made of a woven or knitted fabric.

As techniques for providing a wiring in the wearable biological information measuring device, a method including masking a region other than a region where the wiring is to be disposed on a fabric, and then applying a conductive polymer-containing paint to the fabric (Patent Document 1), and a method in which a silver paste layer sandwiched between urethane resin layers is formed on a fabric (Non-Patent Document 1) are proposed.

RELATED ART DOCUMENTS

Patent Documents

Patent Document 1: JP-A-2014-151018

Non-Patent Documents

Non-Patent Document 1: Gordon Paul et al., Meas. Sci. Technol. 25 (2014)

DISCLOSURE OF THE INVENTION

Problems to be Solved by the Invention

However, the garment provided with the wiring formed by the method described in Patent Document 1 has had problems in that if the fabric is stretched when actually being worn, the wiring cannot follow the elongation of the fabric, and cracks may be produced in a cured product of the conductive polymer for forming a conductive layer, resulting in an interruption or block of electrical continuity. Furthermore, in the conductive fabric produced by the method described in Patent Document 1, since the conductive polymer-containing paint might permeate the inside of the fabric, it was hard to secure a satisfactory thickness of the conductive layer successively formed on the fabric, and although electrical conductivity required for an electrode was able to be achieved, it was difficult to achieve a high electrical conductivity demanded for a wiring.

The garment provided with the wiring formed by the method described in Non-Patent Document 1 also has had problems in that if the fabric is stretched when actually being worn, the wiring cannot follow the elongation of the fabric, and cracks may be produced in the silver paste layer for forming a conductive layer, resulting in an interruption or block of electrical continuity. Even if cracks are produced in the conductive layer, there may be a case where electrical continuity can be provided by accidentally avoiding the cracks, and good electrical conductivity can be confirmed. However, since a defective rate (a ratio of occurrence of interruption or block of electrical continuity) becomes high when cracks are produced, it is impossible to endure mass production.

The present invention has been made by focusing on the above situation, and an object of thereof is to provide a conductive fabric capable of maintaining high electrical conductivity even upon being stretched and a wearable biological information measurement device using the same.

Solutions to the Problems

The conductive fabric of the present invention, which can accomplish the object described above, comprising a fabric and a wiring provided on the fabric, wherein the wiring comprises a first insulating layer formed on the fabric, a conductive layer provided on the first insulating layer, and a second insulating layer provided on the conductive layer, and wherein in a stretching test in which the conductive fabric is stretched by a stretching rate of 10% in a stepwise manner up to a stretching rate of 100% in a longitudinal direction of the wiring, a resistance change ratio when stretched at a stretching rate of 100% is 100-fold or less, the resistance change ratio when stretched at a stretching rate of 100% being represented by an equation: $R_{100}/R_0$ (fold), where $R_0$ is a resistance value at a stretching rate of 0% and $R_{100}$ is a resistance value when stretched at a stretching rate of 100%.

Preferably, in the conductive fabric of the present invention, wherein the conductive layer comprises a conductive filler and a resin.

In a preferred embodiment of the conductive fabric of the present invention, wherein when the number of tests in which a break in electrical continuity occurs when the stretching test is performed 10 times is represented by an alphabet "a", a defective rate represented by an equation: $(a/10) \times 100(\%)$ is 30% or less.

The present invention further includes a wearable biological information measurement device produced using the conductive fabric of the present invention described above. Preferably, the wearable biological information measurement device described above comprising measurement means for measuring biological information of a wearer and a mechanism for analyzing the measured biological information.

Effects of the Invention

According to the conductive fabric of the present invention, in a stretching test in which the conductive fabric is stretched by a stretching rate of 10% in a stepwise manner up to a stretching rate of 100% in the longitudinal direction of the wiring, a resistance change ratio becomes 100-fold or less, and high electrical conductivity can be maintained even if the conductive fabric is stretched. Therefore, the wearable biological information measurement device produced using the conductive fabric has good stretchability and can provide an improved comfortable fit when being worn.

MODE FOR CARRYING OUT THE INVENTION

1. Conductive Fabric

The conductive fabric of the present invention has a structure in which a wiring including a first insulating layer, a conductive layer, and a second insulating layer is provided on a fabric.

1.1. Fabric

The fabric is not particularly limited, and woven or knitted fabrics or nonwoven fabrics composed of conventionally known various natural fibers, synthetic fibers, or semisynthetic fibers may be used for the fabric. Knitted fabrics composed of synthetic fibers are preferred, and more preferred are knitted fabrics of 2-way tricot. The thickness of the fabric may be appropriately selected according to application, and is preferably 1200 to 300 µm, and more preferably 1000 to 500 µm. The areal weight of the fabric may be also appropriately selected according to application, and is preferably 250 to 150 g/m$^2$, and more preferably 220 to 170 g/m$^2$.

1.2. First Insulating Layer

In the present invention, a first insulating layer is formed on the above-mentioned fabric. Accordingly, when wearing a garment made of the conductive fabric, moisture that comes from outside of the garment is prevented from reaching the conductive layer through the fabric. Furthermore, although the conductive layer described later in the present invention has good stretchability, if the fabric is made of a material having good stretchability exceeding the stretchability of the conductive layer, it is thought that the conductive layer may be stretched following the elongation of the fabric, resulting in the production of cracks. The first insulating layer also serves as an elongation stopper to suppress the elongation of the fabric and prevent the conductive layer from being excessively elongated.

A resin forming the first insulating layer is not particularly limited as long as the resin has insulating property, and for example, polyurethane resin, silicone resin, vinyl chloride resin, epoxy resins or the like can be preferably used. Among these, polyurethane resin is more preferable in view of adhesive property with the conductive layer. Note that the resin forming the first insulating layer may be used singly, or in combination of two or more thereof.

Examples of the polyurethane resin include polyester resin, polyether resin, polycarbonate resin, and the like. Among these, polyester resin is preferable in view of stretchability of a coat.

The first insulating layer in the present invention can be formed by dissolving or dispersing the above-mentioned insulating resin in an appropriate solvent (preferably water) and applying or printing the resulting solution onto the fabric to form a coat, followed by evaporating and drying the solvent contained in the coat. Here, it is preferred that the viscosity of the insulating resin used be 400 mPa·s or less in order to easily maintain the electrical conductivity when the conductive fabric is stretched.

The thickness of the first insulating layer is preferably 100 to 10 µm, and more preferably 70 to 20 µm. If the first insulating layer is too thin, the insulation effect and the elongation stopping effect may become insufficient. On the other hand, if the first insulating layer is too thick, the stretchability of the fabric may be inhibited, and the thickness of the entire wiring tends to become too thick, whereby wearing feeling may be deteriorated. Note that part of the first insulating layer formed on the fabric is typically impregnated into the fabric, and the thickness described above (the thickness of the first insulating layer) includes the impregnated part into the fabric. The thickness of the first insulating layer excluding the impregnated part is preferably 60 to 2 µm, and more preferably 40 to 5 µm. When "the thickness of the first insulating layer" is simply mentioned in the present specification, it means the thickness of the entire first insulating layer including the impregnated part.

1.3. Conductive Layer

In the present invention, a conductive layer is formed on the first insulating layer. Electrical continuity is ensured by the conductive layer.

The conductive layer preferably contains a conductive filler and a resin.

The conductive filler forming the conductive layer is preferably metal powder. If necessary, the conductive filler may include conductive materials or metal nanoparticles other than the metal powder.

Examples of the metal powder include noble metal powder such as silver powder, gold powder, platinum powder or palladium powder, and base metal powder such as copper powder, nickel powder, aluminum powder or brass powder, as well as plated powder wherein heterologous particles including base metal or inorganic substances such as silica are plated with noble metal such as silver, and base metal powder that is made into alloy using noble metal such as silver. Among these, silver powder and copper powder are preferable from the viewpoint of easily developing high electrical conductivity and of the cost, and it is desired that silver powder and/or copper powder be contained as main ingredient(s) (50% by mass or more). Note that the conductive filler may be used singly, or in combination of two or more thereof.

Preferred shapes of the metal powder include known flakes (scales), spheres, dendrites, aggregates (a shape wherein spherical primary particles are aggregated into a three-dimensional shape), and the like. Among these, metal powder in flakes, spheres or aggregates is particularly preferred.

Particle diameter of the metal powder is preferably 0.5 to 10 µm in terms of an average particle diameter. When the average particle diameter is too large, it may become difficult to form a desired pattern shape when a wiring is formed in a fine pattern. On the other hand, when the average particle diameter is too small, it is not preferred that the metal powder be easily aggregated in the formation of the conductive layer, and the raw material cost increase with decreasing the average particle diameter.

The amount ratio of the metal powder in the conductive filler is preferably 80% by volume or more, more preferably 85% by volume or more, and further preferably 90% by volume or more. If the amount ratio of the metal powder is too small, it may become difficult to develop sufficiently high electrical conductivity. Note that in the present invention, a mass of each ingredient (solid content) is measured, and a volume calculated based on the following equation [(mass of each ingredient)/(specific gravity of each ingredient)] is used to determine "% by volume".

As to the conductive material, for example, a carbon nanotube is preferred, and a carbon nanotube having a mercapto group, amino group, or nitrile group on its surface, or a carbon nanotube that is surface-treated with a rubber having a sulfide bond and/or nitrile group is particularly preferred. Generally, a conductive material itself has strong cohesive force, and in particular, a conductive material having a high aspect ratio as described later has a low dispersibility in the resin. However, when the conductive material has a mercapto group, amino group or nitrile group on its surface or is surface-treated with a rubber having a sulfide bond and/or nitrile group, affinity to the metal powder increases, and an effective electrically conductive network can be formed together with the metal powder, whereby high electrical conductivity can be realized.

A carbon nanotube has a structure wherein a two-dimensional graphene sheet is rolled in a tubular shape. Depending on the layer numbers and the front end shape, it is divided into multi-wall type, single-wall type and horn type. Moreover, depending on the rolling method of the graphene sheet, it is divided into three types which are armchair type structure, zigzag type structure and chiral type structure. In the present invention, any types of carbon nanotubes may be used. The diameter of the carbon nanotube is not particularly restricted, and is preferred to be 0.5 to 200 nm.

A method for introducing a functional group (mercapto group, amino group, or nitrile group) onto the surface of a carbon nanotube is not particularly limited, and known methods such as a method wherein reaction is carried out and introduction is done by means of covalent bond, a method wherein hydrophobic interaction and/or hydrogen bond are/is utilized, a method wherein π-stacking is utilized, and a method wherein electrostatic interaction is utilized may be used.

As to a method for surface-treating a carbon nanotube with a rubber containing a sulfide bond and/or nitrile group, the functional group introduced onto the surface of a carbon nanotube by any of the above-mentioned methods has only to allow to react with a predetermined rubber having a reactive group, so that the predetermined rubber can be attached to the surface of the carbon nanotube.

It is preferred that the conductive material have an aspect ratio of 10 to 10,000. In particular, when the conductive material is a carbon nanotube, the aspect ratio is preferably 20 to 10,000, and more preferably 50 to 1,000. The conductive materials having such aspect ratios can develop higher electrical conductivity.

The amount ratio of the conductive material in the conductive filler is preferably 20% by volume or less, more preferably 15% by volume or less, and further preferably 10% by volume or less. If the amount ratio of the conductive material is too large, it may become difficult to uniformly disperse it in the resin. Moreover, the above-mentioned conductive materials are usually expensive. For these reasons, it is desired to reduce the use amount of the conductive material to the above-mentioned range.

As to the metal nanoparticles, there are exemplified silver, bismuth, platinum, gold, nickel, tin, copper and zinc. The average particle diameter of the metal nanoparticles is preferably 2 to 100 nm. In particular, in view of the electrical conductivity, copper, silver, platinum and gold are preferable, and the metal nanoparticles that contain silver and/or copper as main ingredient(s) (50% by mass or more) are more preferable. The inclusion of the metal nanoparticles is expected to enhance the electrical conductivity, and in addition, contributes to rheology adjustment of a conductive paste used for forming a conductive layer, whereby the printing property can be improved.

The amount ratio of the metal nanoparticles in the conductive filler is preferably 20% by volume or less, more preferably 15% by volume or less, and further preferably 10% by volume or less. If the amount ratio of the metal nanoparticles is too large, the metal nanoparticles tend to easily aggregate in the resin. Moreover, the metal nanoparticles having a small particle diameter as described above are usually expensive. For these reasons, it is desired to reduce the use amount of the metal nanoparticles to the above-mentioned range.

The content of the above-mentioned conductive filler in the conductive layer (that is, the content of the conductive filler in total solid matters in a conductive paste for forming the conductive layer) is preferably 15 to 45% by volume, and more preferably 20 to 40% by volume. If the content of the conductive filler is too small, the electrical conductivity may be insufficient. On the other hand, if the content of the conductive filler is too large, the stretchability of the conductive layer tends to decrease, and cracks are generated upon stretching the resulting conductive fabric. As a result, good electrical conductivity may not be maintained.

The resin forming the conductive layer preferably contains at least a rubber containing a sulfur atom and/or a rubber containing a nitrile group. The sulfur atom and the nitrile group have high affinity to metal, and the rubber has high stretchability whereby the generation of cracks and the like can be avoided even upon being stretched. Therefore, even if the conductive fabric is stretched, the conductive filler can be held in a uniformly dispersed state, and excellent electrical conductivity can be developed. From the viewpoint of a defective rate described later, the rubber containing a nitrile group is more preferable. Note that the resin forming the insulating layer may be used singly, or in combination of two or more thereof.

There is no particular limitation for the rubber containing a sulfur atom as far as it is a rubber or elastomer containing sulfur. The sulfur atom can be contained in a form such as a sulfide bond or disulfide bond in a main chain of a polymer or as a mercapto group in a side chain or terminal of a polymer. Specific examples of the rubber containing a sulfur atom include polysulfide rubber, polyether rubber, polyacrylate rubber, and silicone rubber that contain a mercapto group, sulfide bond or disulfide bond. In particular, polysulfide rubber, polyether rubber, polyacrylate rubber and silicone rubber that contain a mercapto group are preferred. It is also possible to use a resin in which a sulfur-containing compound such as pentaerythritol tetrakis(S-mercaptobutyrate), trimethylolpropane tris(S-mercaptobutyrate), mercapto group-containing silicone oil, etc. is compounded into a rubber having no sulfur atom. As commercial products that may be used as the rubber containing a sulfur atom, "Thiokol (registered trademark) LP" manufactured by Toray Fine Chemical, which is a liquid polysulfide rubber, and the like are preferably given. The content of the sulfur atom in the rubber containing a sulfur atom is preferably 10 to 30% by mass.

There is no particular limitation for the rubber containing a nitrile group as far as it is a rubber or elastomer containing a nitrile group, and an acrylonitrile butadiene copolymer rubber that is a copolymer of butadiene with acrylonitrile is preferably given. As commercial products that may be used as the rubber containing a nitrile group, "Nipol (registered trademark) 1042" manufactured by Nippon Zeon, and the like are preferably given. The content of nitrile group in the rubber containing a nitrile group (in particular, the content of acrylonitrile in the acrylonitrile butadiene copolymer rubber) is preferably 18 to 50% by mass, and more preferably 28 to 41% by mass. When the content of bonding acrylonitrile in the acrylonitrile butadiene copolymer rubber increases, affinity to metal increases but the rubber elasticity contributing to the stretchability rather decreases.

Although it is desired that the resin forming the conductive layer be made of only a rubber containing a sulfur atom and/or a rubber containing a nitrile group, another resin other than the rubber containing a sulfur atom and the rubber containing a nitrile group may be contained as long as the electrical conductivity, the stretchability, and the application property in the formation of a conductive layer are not impaired. When another resin is contained in addition, the total amount of the rubber containing a sulfur atom and/or the rubber containing a nitrile group in all the resins is set to be preferably 95% by volume or more, more preferably 98% by volume or more, and further preferably 99% by volume or more.

The content of the above-mentioned resin in the conductive layer (that is, the amount of the resin solid content in total solid matters in a conductive paste for forming a conductive layer) is preferably 55 to 85% by volume, and more preferably 60 to 80% by volume. If the content of the resin is too small, there is a tendency that the electrical conductivity may increase, but the stretchability may deteriorate. If the content of the resin is too large, there is a tendency that the stretchability may improve, but the electrical conductivity may decrease.

The conductive layer in the present invention may contain an inorganic substance as long as the electrical conductivity and the stretchability are not impaired. As to the inorganic substance, there may be used various kinds of carbide such as silicon carbide, boron carbide, titanium carbide, zirconium carbide, hafnium carbide, vanadium carbide, tantalum carbide, niobium carbide, tungsten carbide, chromium carbide, molybdenum carbide, calcium carbide and diamond carbon lactam; various kinds of nitrides such as boron nitride, titanium nitride and zirconium nitride; various kinds of borides such as zirconium boride; various kinds of oxides such as titanium oxide (titania), calcium oxide, magnesium oxide, zinc oxide, copper oxide, aluminum oxide, silica, and colloidal silica; various kinds of titanate compounds such as calcium titanate, magnesium titanate, and strontium titanate; sulfides such as molybdenum disulfide; various kinds of fluorides such as magnesium fluoride and carbon fluoride; various kinds of metal soaps such as aluminum stearate, calcium stearate, zinc stearate, and magnesium stearate; and others such as talcum, bentonite, talc, calcium carbonate, bentonite, kaolin, glass fiber, and mica. When the inorganic substance as such is added, there may be cases where printing property and heat resistance in the formation of a conductive layer, and further, mechanical characteristics and durability for long time can be enhanced. Note that the inorganic substance may be used singly, or in combination of two or more thereof.

In the conductive layer in the present invention, if need arises, various kinds of additives such as thixotropic property imparting agent, antifoaming agent, flame retardant, tackifier, preventing agent for hydrolysis, leveling agent, plasticizer, antioxidant, ultraviolet absorber, flame retardant, pigment, and dye may be blended. Note that the additive may be used singly, or in combination of two or more thereof.

The conductive layer in the present invention can be formed in such a manner that a composition (conductive paste) where the above-mentioned ingredients are dissolved or dispersed in an appropriate organic solvent is directly applied to or printed on the first insulating layer in a desired pattern to form a coat, and then the organic solvent contained in the coat is evaporated and dried. Alternatively, the conductive layer in the present invention can be formed in such a manner that a conductive paste is applied to or printed on a release sheet or the like to form a coat, the organic solvent contained in the coat is then evaporated and dried to form a sheet-like conductive layer in advance, and the sheet-like conductive layer may be stacked on the first insulating layer in a desired pattern.

As to the organic solvent using in the conductive paste, its boiling point is preferred to be equal to or higher than 100° C. and lower than 300° C., and more preferred to be equal to or higher than 150° C. and equal to or lower than 290° C. When the boiling point of the organic solvent is too low, the solvent may be evaporated in the preparation of a conductive paste or in the formation of a conductive layer using the conductive paste whereby there is such a risk that the ratio of the ingredients constituting the conductive paste is apt to change. On the other hand, when the boiling point of the organic solvent is too high, there is a possibility that the solvent abundantly remains in the coat in case a low-temperature drying step is demanded (such as 150° C. or lower), and hence there is a risk of causing the lowering of electrical conductivity.

Specific examples of the organic solvent using in the conductive paste include cyclohexanone, toluene, isophorone, γ-butyrolactone, benzyl alcohol, Solvesso 100, 150 and 200 (manufactured by Exxon Chemical), propylene glycol monomethyl ether acetate, terpineol, butyl glycol acetate, diamylbenzene (boiling point: 260 to 280° C.), triamylbenzene (boiling point: 300 to 320° C.), n-dodecanol (boiling point: 255 to 259° C.), diethylene glycol (boiling point: 245° C.), ethylene glycol monoethyl ether acetate (boiling point: 145° C.), diethylene glycol monoethyl ether acetate (boiling point: 217° C.), diethylene glycol monobutyl ether acetate (boiling point: 247° C.), diethylene glycol dibutyl ether (boiling point: 255° C.), diethylene glycol monoacetate (boiling point: 250° C.), triethylene glycol diacetate (boiling point: 300° C.), triethylene glycol (boiling point: 276° C.), triethylene glycol monomethyl ether (boiling point: 249° C.), triethylene glycol monoethyl ether (boiling point: 256° C.), triethylene glycol monobutyl ether (boiling point: 271° C., tetraethylene glycol (boiling point: 327° C.), tetraethylene glycol monobutyl ether (boiling point: 304° C.), tripropylene glycol (boiling point: 267° C.), tripropylene glycol monomethyl ether (boiling point: 243° C.), and 2,2,4-trimethyl-1,3-pentanediol monoisobutyrate (boiling point: 253° C.). As to a petroleum hydrocarbon, there may be exemplified AF Solvent No. 4 (boiling point: 240 to 265° C.), No. 5 (boiling point: 275 to 306° C.), No. 6 (boiling point: 296 to 317° C.), and No. 7 (boiling point: 259 to 282° C.), and No. 0 Solvent H (boiling point: 245 to 265° C.) manufactured by Nippon Oil Corporation. Note that the organic solvent may be used singly, or in combination of two or more thereof. The amount of the organic solvent used can be appropriately set such that the conductive paste has a viscosity suitable for printing, etc.

The conductive paste can be prepared by uniformly dispersing the conductive filler in the resin by appropriately using a conventionally-known method for dispersing powder into liquid. For example, metal powder, a dispersion of a conductive material, and a resin solution are mixed, and then the mixture can be uniformly dispersed by an ultrasonic method, mixer method, three-roll mill method, ball mill method or the like. These methods can be used in combination of two or more thereof.

A method for applying or printing the conductive paste onto the first insulating layer is not particularly limited, and for example, a coating method or a printing method such as a screen printing method, a lithographic offset printing method, an ink jet method, a flexographic printing method, a gravure printing method, a gravure offset printing method, a stamping method, a dispensing method or a squeegee printing can be used.

After forming the coat from the conductive paste, in order to evaporate and dry the organic solvent, heating may be carried out under ambient air, under vacuum atmosphere, under inert gas atmosphere, under reductive gas atmosphere, etc. Heating temperature is, for example, within a temperature range of 20 to 200° C., and it can be selected by taking the demanded electrical conductivity, the heat resistance of the fabric or the insulating layer, etc. into consideration.

The thickness of the conductive layer is preferably 150 to 40 µm, and more preferably 100 to 50 µm. If the conductive layer is too thin, there is a possibility that the expansion and contraction of the fabric damages the conductive layer, and hence the electrical conductivity may lower. On the other hand, if the conductive layer is too thick, the stretchability of the fabric may be inhibited, or the thickness of the entire wiring tends to become too thick, whereby wearing feeling may be deteriorated.

1.4. Second Insulating Layer

In the present invention, a second insulating layer is formed on the above-mentioned conductive layer. Accordingly, when wearing a garment produced using the conductive layer so as to arrange the wiring on the inner side (body side) of the garment, moisture such as perspiration or the like generated from the body side is prevented from contacting the conductive layer.

As examples of the resin forming the second insulating layer, the same resins as those exemplified above for the resin forming the first insulating layer can be given, and the same applies to the preferred resins. The resin forming the second insulating layer may be also used singly, or in combination of two or more thereof. The resin forming the first insulating layer and the resin forming the second insulating layer may be the same or may be different. However, it is preferred that they be the same in respect of reliable covering of the conductive layer and also in respect of preventing the conductive layer from being damaged due to uneven stress arising between the first insulating layer and the second insulating layer when the conductive fabric expands or contracts. The resin forming the second insulating layer can be formed in the same manner as in the first insulating layer as described above.

The thickness of the second insulating layer is preferably 100 to 10 µm, and more preferably 70 to 20 µm. If the second insulating layer is too thin, the second insulating layer is apt to deteriorate due to the repeated expansion and contraction of the conductive fabric, whereby the insulating effect becomes insufficient. On the other hand, if the second insulating layer is too thick, the stretchability of the fabric may be inhibited, or the thickness of the entire wiring tends to become too thick, whereby wearing feeling may be deteriorated.

It is preferred that the difference between the thickness of the first insulating layer excluding the impregnated part and the thickness of the second insulating layer be small (for example, the difference between the thickness of the first insulating layer excluding the impregnated part and the thickness of the second insulating layer is preferably within 30 µm, and more preferably within 25 µm), and it is more preferred that both thicknesses be the same. By doing this, it is possible to readily prevent the conductive layer from being damaged due to uneven stress arising between the first insulating layer and the second insulating layer when the conductive fabric expands or contracts.

1.5. Features of Conductive Fabric

In a stretching test in which stretching is performed by a stretching rate of 10% in a stepwise manner up to a stretching rate of 100% in the longitudinal direction of the above-mentioned wiring (including the first insulating layer, the conductive layer, and the second insulating layer), the conductive fabric of the present invention has a resistance change ratio when stretched at a stretching rate of 100% of 100-fold or less, preferably 95-fold or less, and more preferably 90-fold or less, the resistance change ratio when stretched at a stretching rate of 100% being represented by the equation: $R_{100}/R_0$ (fold), where $R_0$ is a resistance value at a stretching rate of 0%, and $R_{100}$ is a resistance value when stretched at a stretching rate of 100%. In the case of the conventional conductive fabric, the wire may be usually broken in a stage before the stretching rate reaches 100%, or even if it can be stretched up to a stretching rate of 100%, the electrical conductivity significantly decreases to such an extent that the resistance change ratio exceeds 10,000-fold. In contrast, the conductive fabric of the present invention using the rubber containing a sulfur atom and/or the rubber containing a nitrile group as a resin forming the conductive layer exhibits the feature that the resistance change ratio can be kept to 100-fold or less even when the conductive fabric is stretched up to a stretching rate of 100%. Furthermore, the conductive fabric of the present invention withstands not only stretching under severe conditions (up to 100%) as described above but also repeated stretching. Details of the above-mentioned stretching tests in the present invention will be described in the Examples.

In this specification, the "stretching rate" means a rate represented by "%" of a length of elongation (a length after stretching–a length before stretching) when the length before stretching is taken as 100%. For example, when stretched at a stretching rate of 100%, the length after stretching is twice the length before stretching.

In a preferred embodiment of the conductive fabric of the present invention, when the number of tests in which a break in electrical continuity occurs when the above-mentioned stretching test is performed 10 times is represented by an alphabet "a", a defective rate represented by the equation: (a/10)×100(%) is 30% or less, more preferably 20% or less, and further preferably 10% or less. When the conventional conductive fabric is stretched up to a stretching rate of 100%, cracks are produced in the conductive layer, and the possibility of a break in electrical continuity increases. On the other hand, in the conductive fabric of the present invention, it is possible to suppress the above-mentioned defective rate to 30% or less by using the rubber containing a sulfur atom and/or the rubber containing a nitrile group (preferably using the rubber containing a nitrile group) as a resin forming the conductive layer.

2. Wearable Biological Information Measurement Device

The wearable biological information measurement device of the present invention is produced using the conductive fabric of the present invention as mentioned above, and is preferably produced as a garment using the conductive fabric of the present invention as mentioned above. In this case, the conductive fabric may be used such that the wiring is arranged on the inner side (body side) of the garment or on the outer side of the garment. Such a wearable biological information measurement device has attachability similar to usual garments, and a user can easily measure various biological information by just wearing it.

It is preferred that the wearable biological information measurement device of the present invention include measurement means for measuring biological information of a wearer and a mechanism for analyzing the measured information. The measurement means for measuring biological information and the mechanism for analyzing the measured information are connected by the above-mentioned wiring.

As the measurement means for measuring biological information, for example, when measuring electrocardiogram, two or more electrodes in accordance with a dielectric method can be given, when measuring body temperature, thermocouple or thermistor can be given, and when measuring respiration rate, perspiration or exercise amount, various sensors thereof can be given.

As the mechanism for analyzing the measured information, a conventionally-known analyzer (heart rate monitor, electrocardiograph, thermometer, electroencephalograph, electromyograph, etc.) depending on a purpose may be used, and the mechanism includes transmittance means for transmitting the information to an external analyzer.

The present application claims the benefit of priority based on Japanese Patent Application No. 2015-5384 filed on Jan. 14, 2015. The disclosure of the description of Japanese Patent Application No. 2015-5384 filed on Jan. 14, 2015 is incorporated herein by reference in its entirety.

EXAMPLES

Hereinafter, the present invention will be described more in detail by way of examples, and the present invention is not limited to the following examples. Of course, the present invention can be carried out while changes are appropriately made without departing from the spirit of the foregoing and following descriptions, and these change are all encompassed in the technical scope of the present invention.

Resins for forming insulating layers and conductive pastes used in the following Examples and Comparative Examples were prepared as described below.

[Conductive Paste]

A resin shown in Table 1 was dissolved in diethylene glycol monomethyl ether acetate to prepare a solution. To this solution, a liquid wherein silver particles ("Aggregated silver powder G-35" manufactured by DOWA Electronics, average particle diameter: 5.9 μm) and a surface-treated carbon nanotube (CNT) prepared as necessary by a method described later were uniformly dispersed was added such that the ingredients were compounded at a ratio shown in Table 1, and was then kneaded using a three-roll mill to obtain a conductive paste.

Details of resins shown in Table 1 are as follows.
Nitrile group-containing rubber: "Nipol (registered trademark) 1042" (content of acrylonitrile: 33.3% by mass) manufactured by Nippon Zeon
Sulfur-containing rubber: "Thiokol (registered trademark) LP-23" (content of sulfur: 21.5% by mass) manufactured by Toray Fine Chemical
Polyester: "Vylon (registered trademark) RV630" manufactured by Toyobo The surface-treated carbon nanotube (CNT) was prepared by the following method.

[Preparation of CNT having Acrylonitrile Butadiene Oligomer on its Surface]

50 mg of a multi-wall carbon nanotube (SWeNT MW100, manufactured by South West Nano Technologies; diameter: 6 to 9 nm; length: 5 μm; aspect ratio: 556 to 833) was added to 100 ml of a 0.006 mol/l ethanolic solution of o-phenylphenyl glycidyl ether and subjected to an ultrasonic treatment for 30 minutes. After filtering through a PTFE membrane, washing with ethanol was carried out for several times followed by drying to prepare a carbon nanotube having a glycidyl group on its surface.

Next, the resulting carbon nanotube was added to a tetrahydrofuran solution of Hypro™ 1300×16ATBN, which is an acrylonitrile butadiene oligomer having a terminal amino group (content of acrylonitrile: 18% by mass; amine equivalent: 900; manufactured by Emerald Performance Materials), and subjected to a dispersion treatment for 30 minutes using an ultrasonic treating machine. Furthermore, the resulting solution was heated to 60° C. and subjected to an ultrasonic treatment for one hour, and after filtering through a PTFE membrane, washing with tetrahydrofuran was carried out for several times followed by drying to obtain a carbon nanotube having an acrylonitrile butadiene oligomer on its surface.

[Resin for Forming Insulating Layers]

To 9 parts by mass of polyurethane resin shown in Table 1, 4 parts by mass of a mixture of 1 part by mass of thickener ("ACTGEL AP200" manufactured by Senka, acrylic acid based polymer) and 10 parts by mass of water was added to obtain a resin for forming an insulating layer.

Details of resins shown in Table 1 are as follows.
Polyurethane A: "UREARNO (registered trademark) W600" manufactured by Arakawa Chemical Industries (polyester-based anionic aqueous polyurethane, content of urethane resin: 35% by mass, isopropyl alcohol: 5% by mass, viscosity: 300 to 30 mPa·s (25° C.))
Polyurethane B: "UREARNO (registered trademark) W321" manufactured by Arakawa Chemical Industries (polyester-based anionic aqueous polyurethane, content of urethane resin: 35% by mass, isopropyl alcohol: 9% by mass, viscosity: 1000 to 500 mPa·s (25° C.))

Examples 1 to 6 and Comparative Examples 1 to 3

2-way tricot ("KNZ2740" manufactured by GUNSEN, nylon yarn:urethane yarn=63%:37% (blend ratio), areal weight: 194 g/m$^2$) was prepared as a fabric, and this fabric was cut into a length of 15 cm and a width of 5 cm.

Next, to a region having a length of 15 cm and a width of 3 cm on the cut fabric, the resin for forming an insulating layer shown in Table 1 was applied so that a first insulating layer had a thickness (dry thickness) of 35 μm, and dried in a hot-air drying oven of 100° C. for 20 minutes or longer to form a first insulating layer. The thickness of the first insulating layer excluding part of the first insulating layer impregnated into the fabric was 15 μm.

Next, the conductive paste prepared in accordance with the compounding ratio shown in Table 1 was applied to a release sheet so as to have a dry thickness of 60 μm, and dried in a hot-air drying oven of 120° C. for 30 minutes or longer to make a sheet-like conductive layer with the release sheet. This sheet-like conductive layer with the release sheet was cut into a length of 15 cm and a width of 1 cm, the release sheet was peeled off, and the conductive layer was laminated on the above-mentioned first insulating layer.

Subsequently, to a region having a length of 10 cm and a width of 3 cm enough to cover the laminated conductive layer, the same resin for forming an insulating layer as the resin that was used for forming the above-mentioned first insulating layer was applied so as to have a dry thickness of 35 μm, and dried in a hot-air drying oven of 100° C. for 20 minutes or longer to form a second insulating layer, thereby obtaining a conductive fabric.

The conductive fabric obtained in each Example and Comparative Example was subjected to the following test and evaluated.

out of 10 times of the stretching tests, the average value of the tests performed 9 times is a resistance change ratio at a stretching rate of x %.

[Defective Rate]

When the above-mentioned stretching test is performed 10 times, and the number of tests in which a break in electrical continuity has occurred at any stage up to a stretching rate of 100% is represented by an alphabet "a", a defective rate is a ratio of the number "a" of tests to the total number of tests (10 times) (that is, defective rate=(a/10)×100(%)).

TABLE 1

| | | | Example1 | Example2 | Example3 | Example4 | Example5 | Example6 | Comparative Example1 | Comparative Example2 | Comparative Example3 |
|---|---|---|---|---|---|---|---|---|---|---|---|
| Conductive layer | Conductive filler | Silver particles (% by volume) | 30 | 30 | 27 | 30 | 30 | 30 | 30 | 10 | 50 |
| | | CNT(% by volume) | | 5 | 3 | | 3 | | | | |
| | Resin | Nitrile group-containing rubber (% by volume) | 70 | 65 | 70 | | | 70 | | 90 | 50 |
| | | Sulfur-containing rubber (% by volume) | | | | 70 | 67 | | | | |
| | | Polyester (% by volume) | | | | | | | | 70 | |
| First insulating layer Second insulating layer | Resin (polyurethane) species | | A | A | A | A | A | B | A | A | A |
| Resistance change ratio (fold) | | stretching rate 10% | 1.3 | 1.1 | 1.3 | 1.4 | 1.3 | 1.3 | 1.3 | 1.5 | 1.8 |
| | | stretching rate 20% | 1.7 | 1.2 | 1.9 | 2.8 | 2.3 | 2.9 | — | 7.7 | 3.6 |
| | | stretching rate 50% | 5.9 | 2.3 | 7.2 | 9.5 | 8.1 | 7.7 | — | 65.3 | 24.6 |
| | | stretching rate 80% | 18.5 | 12.7 | 23.9 | 35.2 | 43.3 | 26.0 | — | — | 155.6 |
| | | stretching rate 100% | 51.4 | 38.4 | 69.6 | 82.5 | 90.5 | 80.8 | — | — | 10725 |
| | | Defective rate(%) | 0 | 10 | 0 | 20 | 20 | 20 | 100 | 100 | 40 |

<Stretching Test>

Using a stretch tester (a hand-rotated drawer) provided with two chucks having a width of 2.5 cm, the conductive fabric was held with a distance of 5 cm between the chucks and stretched by a stretching rate of 100% in the longitudinal direction of the wiring. At this time, using Digital Multimeter ("YOKOGAWA TY530" manufactured by Yokogawa Meters & Instruments), resistance values (Ω) were measured for every displacement amount (5 cm×10%=0.5 cm) corresponding to a stretching rate of 10% in an outer side of opposite two chucks (measurement distance: 10 cm). The measurement of resistance values was conducted immediately after stretching (within three seconds), and a subsequent stretching was restarted after three minutes. Note that the resistance value was confirmed for every stretching rate of 10%, and when a break in electrical continuity occurred at any stage up to 100% stretching, any more measurement was not performed.

[Resistance Change Ratio]

The resistance change ratio at each stretching rate of x % is a ratio of a resistance value ($R_x$) at a stretching rate of x % to a resistance value ($R_0$) at a stretching rate of 0% (that is, resistance change ratio=$R_x/R_0$ (fold)). After performing the above-mentioned stretching test 10 times, the average value thereof was used. Note that among the stretching tests of 10 times, the tests in which a break in electrical continuity had occurred were not counted because it was impossible to measure the resistance values ($R_x$). Specifically, for example, when a break in electrical continuity occurs once

The invention claimed is:

1. A conductive fabric comprising a fabric and a wiring provided on the fabric,
   wherein the wiring comprises a first insulating layer formed on the fabric, a conductive layer provided on the first insulating layer, and a second insulating layer provided on the conductive layer,
   wherein the conductive layer comprises a conductive filler and a resin,
   wherein the fabric is a woven fabric, a knitted fabric, or a nonwoven fabric, and
   wherein in a stretching test in which the conductive fabric is stretched by a stretching rate of 10% in a stepwise manner up to a stretching rate of 100% in a longitudinal direction of the wiring, a resistance change ratio when stretched at a stretching rate of 100% is 100-fold or less, the resistance change ratio when stretched at a stretching rate of 100% being represented by an equation: $R_{100}/R_0$ (fold), where $R_0$ is a resistance value at a stretching rate of 0% and $R_{100}$ is a resistance value when stretched at a stretching rate of 100%.

2. The conductive fabric according to claim 1, wherein when the number of tests in which a break in electrical continuity occurs when the stretching test is performed 10 times is represented by an alphabet "a", a defective rate represented by an equation: (a/10)×100(%) is 30% or less.

3. A wearable biological information measurement device produced using the conductive fabric according to claim 1.

4. The wearable biological information measurement device according to claim 3 comprising measurement means for measuring biological information of a wearer and a mechanism for analyzing the measured biological information.

5. The conductive fabric according to claim 1, wherein the fabric is a knitted fabric.

* * * * *